United States Patent
Maiorella

[11] Patent Number: 5,096,816
[45] Date of Patent: Mar. 17, 1992

[54] IN VITRO MANAGEMENT OF AMMONIA'S EFFECT ON GLYCOSYLATION OF CELL PRODUCTS THROUGH PH CONTROL

[75] Inventor: Brian L. Maiorella, Oakland, Calif.

[73] Assignee: Cetus Corporation, Emeryville, Calif.

[21] Appl. No.: 533,688

[22] Filed: Jun. 5, 1990

[51] Int. Cl.$^5$ .................. C12P 21/08; C12N 5/12; C12N 5/02
[52] U.S. Cl. .................. 435/70.21; 435/240.27; 435/240.31
[58] Field of Search ............... 435/70.3, 240.3, 240.31, 435/29, 70.21, 240.27, 240.31; 530/380, 395

[56] References Cited

U.S. PATENT DOCUMENTS 4,879,222  11/1989  Alderman et al. ............ 435/240.31

OTHER PUBLICATIONS

Thorens, et al. Chloroquime and Ammonium Chloride Prevent Terminal Glycosylation of Immunoglobulins in Plasma Cells . . . Nature vol. 321, pp. 618–620, Jun. 5, 1986.

Dean et al. Effects of Exogenous Amines on Mammalian Cells, with Particular Reference to Membrane Flow Biochemical Journal vol. 217, pp. 27–40, 1984.

Primary Examiner—Elizabeth C. Weimar
Assistant Examiner—George C. Elliott
Attorney, Agent, or Firm—Gregory J. Giotta; Wean Khing Wong

[57] ABSTRACT

This invention relates generally to the field of cell culture. The invention presents pH based methods for controlling the glycosylation patterns of cell products, particularly proteins produced by cells in vitro, preferably via a multi-level pH control strategy. Preferably, this invention is applied to manage the effect of high level of ammonia on the glycosylation of cell products. The glycosylation affected is preferably that of terminal sialylations of the oligosaccharide of glycoproteins.

2 Claims, No Drawings

IN VITRO MANAGEMENT OF AMMONIA'S EFFECT ON GLYCOSYLATION OF CELL PRODUCTS THROUGH PH CONTROL

FIELD OF THE INVENTION

This invention relates generally to the field of cell culture. The invention presents pH based methods for controlling the glycosylation patterns of cell products, particularly proteins produced by cells in vitro, preferably via a multi-level pH control strategy. Preferably, this invention is applied to manage the effects of high levels of ammonia on the glycosylation of cell products. The glycosylation affected is preferably that of terminal sialylation of the oligosaccharides of glycoproteins.

BACKGROUND OF THE INVENTION

Since this invention relates to the effects of external (culture medium) ammonia and pH on the glycosylation of cell products produced by cell culture, the following discussion presents the background on traditional cell culture methods and selection of pH, the effects of glycosylation of a cell product, and the investigations into pH and ammonia on the nature of the cell products.

Traditional Methods for Growing Cell Culture and Criteria for Selecting pH of the Culture Medium Traditionally, the pH of a culture medium is manipulated with the goal of achieving maximum cell growth and/or production. Media for cell culture are typically prepared with pH adjusted to 7.4 (similar to human blood pH). The optimum pH for growth is cell line dependent, and is typically in the range 6.9–7.6 (reviewed in Eagle H., 1973, *J Cell Physiol*, 82: 1–8). The pH level traditionally used for large scale culture of mammalian cells is typically between 7.2 to 7.4 (reviewed in R. C. Telling and P. J. Radlett, "Large-Scale Cultivation of Mammalian Cell," in *Advances in Applied Microbiology*, Academic Press, New York, 1970, 13: 91–117) which is determined to favor good cell growth. Optimum pH for growth of lymphoblastoid cell lines has been reported in the pH range 7.05–7.4 (Harbour, C. et al., 1989, "pH Control Options for Hybridoma Cultures," *Biotechnology Techniques*, 3(2): 73–78) or 7.25–7.5 (Birch, J. R. et al., 1980, "The Effect of pH on the Growth and Carbohydrate Metabolism of a Lymphoblastoid Cell Line," *Develop. Biol. Standard.*, 46: 59–63). Thus, the effect of pH on cell growth or production, and not its effect on the nature of a cell product has been the determining factor in selecting pH in traditional cell culture.

For example, the prior art has disclosed varying the pH, glucose, and lactate production in the growth and production phases of the cell culture to optimize growth and production respectively. "Method of Culturing Cells", Endotronics, Inc., Int'l Publication No. WO 88/01643, Int'l Pub. date: Mar. 10, 1988 (U.S. priority date Aug. 29, 1986). Significantly, this reference does not examine the nature of the cell products produced. It also does not examine the effect of high levels of ammonia on the nature of the cell products, especially their glycosylation patterns. Further, the interaction of pH and ammonia on the glycosylation pattern of the cell products, and methods for increasing the production of a cell product with the desired glycosylation pattern are not addressed.

The Effect of Glycosylation of a Cell Product and Investigations into the Effects of Ammonia and pH on such Glycosylation The glycosylation pattern of a product can affect its chemical or biological functions (Reviewed in Rademacher, T. W., et al., 1988, "Glycobiology," *Ann. Rev. Biochem.*, 57: 785–838). For example, it has generally been found that products are processed by the human liver differently, i.e. at a different hepatic clearance rate, depending on the degree of glycosylation, the specific site(s) glycosylated, and the specific oligosaccharide composition and linkage structure. In the case of a therapeutic product, such slower clearance has the advantage of allowing the product sufficient time to exert an effect on the human system. In the case of an antibody, treatment utilizing such antibody would require lower doses of the antibody with less frequent administrations to maintain protective serum levels. On the other hand, antibodies which clear rapidly from circulation are useful, for example, in the case of imaging and tumor therapy, where the antibodies are administered regionally to a target tumor, and it is desirable to quickly clear the antibodies when they reach the bloodstream because they have undesired side-effects or to prevent them from binding to tissue outside the tumor area and giving a false positive signal.

The human liver contains specific glycoprotein receptors on hepatocytes which bind certain terminal glycosides and initiate their clearance from circulation. (Ashwell, G., et al., 1982, *Ann. Rev. Biochem.*, 51: 531–554, and Ciechanover, A. et al., 1983, "The Asialoglycoprotein Receptor Internalizes and Recycles Independently of the Transferrin and Insulin Receptors," *Cell*, 32: 267–275). Thus, the clearance of a protein can be accelerated by conjugating the protein to a glycoside that binds to the glycoprotein receptor or by exposing the glycoside existing in a glycoprotein as a terminal residue. Galactose and glucose are terminal sugar residues generally recognized by the glycoprotein receptor. Thus, for example, a therapeutic product which has a terminal sialic acid linked to a galactose residue would have cleared faster if the sialic acid residue is removed, thereby exposing a terminal galactose residue to the glycoprotein receptor. Conversely, if sialic acid is added to the terminal galactose residue, the glycoprotein would have cleared less rapidly.

In addition to their effect on clearance rate, the oligosaccharide moieties are sometimes significant in determining the biological specific activity, i.e. the activity per gram, of glycoproteins (reviewed in Goochee, C. F. et al., May 1990, "Environmental Effects on Protein Glycosylation," *Bio/Technology.*). For example, glycosylation can significantly affect the biological specific activity of a number of pituitary and placental glycoprotein hormones towards their target cells.

Further, the in vivo biological activity of some proteins may be controlled through modulation of their glycosylations. For example, recent studies suggest that glycoproteins IgE potentiating factor (IgE-pF) and IgE suppressive factor (IgE-sF) may have the same protein core structure. When IgE-pF is treated with neuraminidase, its biological specific activity is lost, this suggests that terminal sialic acid residues are necessary for IgE-pF potentiating activity. Id.

Oligosaccharide moieties also affect the biological specific activity of immunoglobulins. For instance, the effectiveness of Fc receptor binding and complement activation by IgG and IgM are dependent on glycosylation in the heavy chain. Id. Glycosylation in the variable residue of a monoclonal antibody can affect antibody binding affinity (Wallick S. L., et al., 1988, *J. Exp. Med.*, 168: 1099-1109).

Another example of the effect of glycosylation is seen in the glycoprotein, extrinsic tissue plasminogen activator (tPA) which binds fibrin. Cells produce tPA in two forms, I and II, which differ in the number of attached oligosaccharides. Types I and II tPA have three and two N-linked oligosaccharides, respectively. Both types have similar kinetic constants in amidolytic assays, using small chronogenic substrates. However, they differ in the rate at which they form an active complex with fibrin. When the oligosaccharides are removed, tPA cleaves plasminogen in the absence of fibrin, although the affinity for fibrin is unchanged (reviewed in Rademacher, R. B., "Glycobiology," supra).

Another example involves the glycoprotein human granulocyte/macrophage colony stimulating factor (hGM-CSF). When hGM-CSF is produced from a recombinant source (in *Escherichia coli*) in which no glycosylation occurs, the molecule exhibits the in vivo activities of the native form but it does not stimulate erythroid-burst promoting activity. Id.

Several factors have been identified which affect in vitro glycosylation, as reviewed in A. Elbein, 1987, "Inhibitors of the Biosynthesis and Processing of N-linked Oligosaccharide Chains", *Ann. Rev. Biochem.*, 56: 497-534, and Goochee, C., et al., supra. These factors include: 1) glucose starvation, 2) hormonal effects including thyrotropin releasing hormone and retinoic acid, 3) chemical effects including carbonyl cyanide m-chlorophenylhydrazone and EDTA, and 4) growth factors.

Significantly, hitherto the interaction between pH and ammonia, on the nature of cell products has not been investigated nor observed. As shown below, there have been investigations into the effects of ammonia or pH on the sialylation of proteins. However, these investigations did not determine how ammonia interacts with pH to affect glycosylation. Thus, these investigations did not determine how pH may interact with high level of ammonia to affect the glycosylation pattern, and especially terminal sialylations of a cell product. The effect of pH on sialylation of glycocerebrosidase has been investigated into without considering the ammonia effect. (See Aerts, below) The effect of ammonia on sialylation has been investigated but not the interaction of pH in altering this effect. (See Thorens, et al., below) The other references have failed to utilize tests that would determine the degree of sialylations as affected by ammonia alone (see McQueen et al., below) or pH in combination with ammonia (see Rothman, et al., below). The following discuss these references in more detail.

10 mM of ammonium chloride has been observed to inhibit terminal sialylation of immunoglobulins produced by plasma cells. Thorens, B., et al., 1986, "Chloroquine and Ammonium Chloride Prevent Terminal Glycosylation of Immunoglobulins in Plasma Cells Without Affecting Secretion," *Nature*, 321:618, Thorens et al. demonstrated that 10 mM chloroquine inhibited the activity of sialyltransferase (as a plasma membrane preparation) by 30-40%. Variation of the pH from 5.8 to 7.0 in the absence or presence of chloroquine had no effect on the activity of sialytransferase.

McQueen and Bailey examined the effects of ammonium ion and pH on hybridoma metabolism, McQueen, A. et al., 1990, "Effect of Ammonium Ion and Extracellular pH on Hybridoma Cell Metabolism and Antibody Production," *Biotechnol. Bioeng.*, 35: 1067-1077. These researchers conclude that both decreases in external (medium) pH and increases in external (medium) $NH_4Cl$ concentration lead to decreased intracellular (cytoplasmic) pH. Though they looked at the specific antibody production rates as a function of pH and $NH_4Cl$, these researchers did not investigate nor observe the interaction of pH and ammonia on the nature/quality of the cell products. Instead, they conclude that $NH_4Cl$ (added to 10 mM) had no effect ("to a first approximation") on the quality of antibody produced since there was no difference in gel electrophoresis mobilities. These researchers did not compare the effects of high and low pH in the presence of a high (for example 10 mM) concentration of ammonium. Rothman, R. J., et al., 1989, "Clonal Analysis of the Glycosylation of Immunoglobulin G," *Biochemistry*, 28, 1377-1384, present data indicating an increase in the size heterogeneity of oligosaccharides from an antibody produced at pH significantly above or below normal culture pH of 7.2. All the data is for cultures grown in the presence of only low levels of ammonia, and no data is presented regarding the effect of pH on the degree of sialylation.

J.M.F.G. Aerts reports that an external pH of 7.6 is a critical value for the culture of K562 erythroblastoid cells, above which the oligosaccharides of glycocerebrosidase are markedly less sialylated than at normal culture pH. No analysis is presented of the effect of ammonia on sialylation. "Manipulation of Lysosome Biogenesis in Cultured Blastoid Cells", p. 273-299 in *Biochemical Studies on Glycocerebrosidase in Relation to Gaucher Disease*, University of Amsterdam, The Netherlands. (Thesis) (1988).

The effect of high level of ammonia on the glycosylation of cell products, in particular proteins, produced from cell culture is hitherto not at issue nor investigated into due to the fact that the traditional culture media contain low level of glutamine and alanine. The typical cell culture media compositions contain 2 or 4 mM of glutamine, in standard serum supplemented and serum-free medium formulations. Ian Freshney, Culture of Animal Cells - A Manual of Basic Technique, Alan R. Liss, New York, 1987. (For typical basal media compositions for use in both serum containing and serum-free media, see Table 7.5 and 7.6 at pg. 74-78, Id.) The ammonia level produced in these media due to cell metabolism and spontaneous degradation of glutamine typically ranges from 1 to 6 mM.

Unlike the traditional culture media, the culture media (with or without nutrient feeds and reagents) disclosed in pending U.S. patent application, Ser. No. 248,634, filed Sept. 23, 1988, W. Howarth, et al., "Cell Culture Medium for Enhanced Cell Growth, Culture Longevity and Product Expression," contains high level of glutamine and/or alanine. Applicant is a co-inventor of this U.S. patent application. (The culture media, nutrient feeds and reagents are hereinafter referred to as applicant's culture media, nutrient feeds and reagents.) Whereas applicant's culture media nutrient, feeds and reagents allow increased production of cell products, in particular that of antibody, their high levels of glutamine and/or alanine cause the production of high level of ammonia. At this high level, applicant believes that the ammonia affects the glycosylation, in particular, the high level of ammonia inhibits the terminal sialylation of the cell products.

SUMMARY OF THE INVENTION

One aspect of the invention presents methods for controlling the effect of high levels of ammonia on the glycosylation pattern of cell products, preferably terminal sialylation of oligosaccharides of glycoproteins, consisting of manipulating the pH of the culture medium.

Another aspect of the invention presents a multi-level pH strategy for controlling the effect of high levels of ammonia on the glycosylation patterns of cell products, preferably the terminal sialylation of the oligosaccharides of glycoproteins.

A further aspect of the invention presents cell products with desired glycosylation patterns, preferably having controlled terminal sialylation.

DETAILED DESCRIPTION OF THE INVENTION

The invention described herein draws on previously published work and pending patent applications. By way of example, such work consists of scientific papers, patents or pending patent applications. All of these publications and applications, cited previously or below are hereby incorporated by reference.

The applicant believes that high level of ammonia in a cell culture, preferably at about 6 mM and above, has an effect on the glycosylation of the cell products produced by the cell culture. This effect is believed to be more pronounced at ammonia levels of about 8 mM and above. An example of the glycosylation pattern affected by high level of ammonia is the reduction in the terminal sialylations of the oligosaccharides of a cell product. Hitherto, the level of ammonia produced in traditional media is insignificant to cause a significant change in the glycosylation pattern of a cell product. Thus, the interaction between the pH and ammonia level on the nature of the cell products has not been reported. Further, investigations into the effects of ammonia and pH have not realized that these two factors interact to affect the glycosylations of cell products, in particular, the terminal sialylations of cell proteins (see Background of the Invention). Due to their high ammonia production level, applicant's culture media, nutrient feeds and reagents, disclosed in U.S. patent application, Ser. No. 248,634 first posed the novel problem of high ammonia level affecting glycosylation of cell products.

Additionally, the effect of pH on the nature of a cell product has not been applied as the basis to select pH for cell growth in traditional cell culture. As discussed in the Background of the Invention, the traditional criteria for selecting pH in a cell culture is to optimize cell growth and/or production, without examining the nature of the cell products. This invention departs from the prior art in teaching the manipulation of pH to overcome the effect of ammonia and to affect the nature of a cell product. By the traditional criteria for selecting pH, the pH which the present invention determines would promote terminal sialylation of a protein, in the presence of high level of ammonia, would not be a pH of choice because cell growth at this pH is not optimal (see Harbour, C., supra., in which pH of 6.75 was shown to be non-optimal for cell growth and viability). Having placed the invention in relation to the prior art, the following presents a detailed description of the invention.

Glycosylation patterns may take into account the site(s), the type of glycoside residue added; or the type of glycoside residue exposed if a terminal glycoside is removed; and the extent of glycosylation or non-glycosylation of the cell product. Preferably, the glycoside is a terminal sialic acid residue.

A cell culture typically goes through different growth phases which include: post inoculation (lag), exponential growth, pseudo-stationary and death. The following defines some of the terms:

"Growth phase" of a cell culture is defined as the phase of the culture wherein viable cell number is substantially increasing.

"Production phase" is defined as the phase wherein the cells are placed in an environment for the specific purpose of maintaining the viable cell population and for the production of a cell product and not necessarily optimized for cell growth or proliferation.

"Pseudo-stationary phase," is defined as the phase where viable cell density is relatively constant, due to roughly matching low levels of growth and death rates.

"Protein" is hereby defined to include glycoprotein.

This invention presents methods for in vitro production of cell products with a desired glycosylation pattern. More preferably, the desired glycosylated cell products are produced by manipulating the pH of the cell culture. In the preferred embodiment, this invention presents methods for obtaining the desired glycosylated cell products by means of managing the effect of high levels of ammonia on the glycosylation of these cell products. The methods are preferably used in cell culture containing a high level of ammonia.

The invention presents methods for utilizing low pH to minimize the inhibition of terminal sialylation of cell products by high levels of ammonia. More preferably, the methods are applied to minimize the inhibition of terminal sialylation of proteins produced in cell culture in the presence of high levels of ammonia. This invention also includes the desired glycosylated products and the cells produced by the methods presented herein. Preferably, the cell products are proteins which contain terminal sialylations when produced in a culture containing high levels of ammonia.

The methods are applicable to a variety of cells for obtaining a broad range of products. For the purpose of illustrating altered glycosylation pattern of cell products realized by the invention herein, the alterations of the terminal sialylation pattern of monoclonal antibodies secreted by the hybridoma T88 is shown.

A variety of culture media may be used. Preferably, the culture media are those producing high levels of ammonia, preferably ammonia levels at or above about 6 mM. The most preferred media are those producing ammonia level at or above about 8 mM. Examples of the preferred media are those disclosed in, or containing the primary supplements and/or class I reagents of U.S. patent application Ser. No. 248,634, filed Sept. 23, 1988, W. Howarth, et al., "Cell Culture Medium for Enhanced Cell Growth, Culture Longevity and Product Expression," supra. The ammonia levels produced depend on the media, supplements and/or class I reagents and the length of time the cell culture grow in these media. Further, the level of ammonia produced and the maximum level of ammonia tolerable by the cells in a particular culture medium are cell line dependent. Since the media, supplements and/or class I reagents disclosed in the above patent application contain higher amount of glutamine and/or alanine than the traditional media, the levels of ammonia produced by cells grown in them are correspondingly higher than found in the traditional culture media.

The most preferred culture medium for this invention is DM21 which contains high glutamine content and produces about 8 mM and above of ammonia. The composition of DM21 is presented below in Table 1. In the case of the hybridoma T88, it has been shown that the hybridoma produced up to 30–40 mM of ammonia in modifications of DM21 medium containing additional glutamine and other nutrients. At these high levels of ammonia, the hybridoma still maintained viable cell density and produced antibodies T88. It is projected that the hybridoma T88 could tolerate up to 60 mM of ammonia and still maintain viable cell density and produce antibodies T88.

TABLE 1

| | Composition of DM21 | |
|---|---|---|
| | Component | Mg/L |
| 1. | Arginine | 500.0000 |
| 2. | Arginine.HCL | 42.0000 |
| 3. | Asparagine | 178.4000 |
| 4. | Aspartate | 60.0000 |
| 5. | Glutamate | 60.0000 |
| 6. | Glycine | 70.0000 |
| 7. | Histidine | 107.5000 |
| 8. | Histidine.HCL.H$_2$O | 21.0000 |
| 9 | Hydroxyproline | 10.0000 |
| 10. | Isoleucine | 327.4000 |
| 11. | Leucine | 327.4000 |
| 12. | Lysine.HCL | 343.1000 |
| 13. | Methionine | 122.5000 |
| 14. | Phenylalanine | 140.5000 |
| 15. | Proline | 60.0000 |
| 16. | Serine | 136.0000 |
| 17. | threonine | 207.6000 |
| 18. | Tryptophan | 110.5000 |
| 19. | tyrosine.2Na.2H$_2$O | 216.0000 |
| 20. | Valine | 206.8000 |
| 21. | pAminobenzoic Acid | 0.5000 |
| 22. | Biotin | 0.1000 |
| 23. | Ca Pantothenate | 2.1250 |
| 24. | Folic Acid | 2.5000 |
| 25. | Nicotinamide | 2.5000 |
| 26. | Pyridoxal.HCL | 2.0000 |
| 27. | Pyridoxine.HCL | 0.5000 |
| 28. | Riboflavin | 0.3000 |
| 29. | Thiamine.HCL | 2.5000 |
| 30. | Vitamin B12 | 0.0025 |
| 31. | Ca(NO$_2$)$_2$.H$_2$O | 50.0000 |
| 32. | KCl | 400.0000 |
| 33. | MgSO$_2$.7H$_2$O | 150.0000 |
| 34. | NaCl | 5000.0000 |
| 35. | NaH$_2$PO$_4$.H$_2$O | 830.0000 |
| 36. | Na$_2$HPO$_4$.7H$_2$O | 360.0000 |
| 37. | Glucose | 5250.0000 |
| 38. | Glutathione (Reduced) | 0.5000 |
| 39. | Na Pyruvate | 110.0000 |
| 40. | NaHCO$_3$ | 2850.0000 |
| 41. | Phenol Red | 10.0000 |
| 42. | Choline Chloride | 43.5000 |
| 43. | Inositol | 41.0000 |
| 44. | FeCl$_3$.6H$_2$O | 2.7000 |
| 45. | Fe(NO$_3$)$_3$.9H$_2$O | 0.0500 |
| 46. | (NH$_4$)$_6$ Mo$_7$O$_{24}$ | 0.1000 |
| 47. | CoCl$_2$.6H$_2$O | 0.1000 |
| 48. | CuCl$_2$.2H$_2$O | 0.1000 |
| 49. | MnCl$_2$.4H$_2$O | 0.1000 |
| 50. | ZnCl$_2$ | 0.1000 |
| 51. | Na$_2$SeO$_3$ | 0.0200 |
| 52. | Na Citrate.2H$_2$O | 294.1000 |
| 53. | HEPES | 2979.0000 |
| 54. | Cystine | 199.0000 |
| 55. | Ethanolamine | 10.0000 |
| 56. | Monothioglycerol | 1.0000 |
| 57. | Glycerol | 200.0000 |

TABLE 1-continued

| | Composition of DM21 | |
|---|---|---|
| | Component | Mg/L |
| 58. | Insulin | 5.0000 |
| 59. | Transferrin | 5.0000 |
| 60. | Selenous Acid | 0.0050 |
| 61. | Pluronic Polyol F68 | 1000.0000 |
| 62. | Glutamine | (8–40 mM) |

In this invention, the pH of the culture medium is maintained at a pH which is preferably about the optimal pH for which maximum production of the desired products in the desired glycosylated form is obtained. The optimal pH which favors the desired glycosylated form of a cell product may vary from one cell line to another. The methods therefore involve first determining the optimal pH at which the maximum amount or maximum percentage of the desired product in the desired glycosylated form is produced. To do so, the cells are grown in several different constant pH cultures. These single level pH cultures can be conducted in simple fed-batch conditions that result in high cell density, prolonged production phase, and high ammonia concentration during the production phase. These cells are grown in pHs ranging between the maximum to the minimum pHs at which reasonable cell growth is still possible.

The concentrations of the ammonia and cell product of interest from these cultures are then analyzed. The degree and pattern of glycosylation of the cell product can be determined by methods known to a person of ordinary skill in the art. Thus, the optimal pH is determined for a culture medium, at a certain ammonia level, at which the desired glycosylation pattern is obtained.

On the other hand, the pH which optimizes cell growth does not necessarily optimize product expression. This may occur when the growth and production phases do not overlap. For example, for certain cell lines, the production phase is the pseudostationary and death phase during which the majority of the product is produced, instead of the growth phase. In these cell lines, the specific production rate per cell is enhanced during the stationary and death phase. Depending on the particular cell line, a different pH may be optimal for each of these phases for maximum overall growth, longevity, or product expression.

With the above in view, the preferred embodiment presents a multi-level pH control strategy. In this method the cells are first grown, during the growth phase, at about a pH which provides optimal cell growth. The preferred pH is the pH which provides maximum cell growth or minimum lag phase. At the production phase, the pH of the cell culture is changed to about a pH which favors production of the desired product in the desired glycosylated form. Preferably, as the culture approaches production phase, the pH is gradually ramped (changed) to about a pH which is optimal for the production of the desired glycosylated products. The preferred pH is the pH which is optimal for production of the desired glycosylated product. The gradual ramping of pH during inter-phase transition avoids the detrimental effect of rapid pH shifts on the cells.

To execute the multi-level pH control stragety, the respective optimum pHs for the cell culture in the growth and production phases are first determined. As described above, the cells are grown in several different constant pH cultures. Additionally, the optimum pH for cell growth is determined at about the point of maximum growth or minimum lag phase. This can be determined using methods known in the art. Thus, in the preferred embodiment of the multi-level pH control strategy, the cells are initially grown under conditions that provide good growth. During the exponential growth, the goal is to extend the exponential growth to maintain growth to high densities. Once a reasonable cell density is achieved, the pH is gradually ramped to one that results in the production of the desired product in the desired glycosylated form. This pH is maintained during the production phase. The goal of the production phase is to maximize cell survival at high cell density for an extended pseudo-stationary phase for prolonged production, while maintaining a high production of the desired glycosylated cell product. Preferably, to minimize nutrient limitation, appropriate nutrient is fed to the culture during the course of the culture.

It should be noted that in both methods, the optimal pH for obtaining the desired glycosylated cell products can be varied to accommodate cell growth and viability, and vice versa. For example, at the cost of reduced cell longevity, growth or viability, a different pH may be maintained to maximize the production of the desired product in the desired glycosylated form. Since the optimal pH for cell growth and viability may differ depending on the cell line, the optimal pH for obtaining a glycosylated, in particular a sialylated cell product while maintaining satisfactory growth may correspondingly differ depending on the cell line. The preferred pH for maximizing the growth of hybridoma T88 is about pH 7.2. The preferred pH range for achieving terminal sialylation of the monoclonal antibodies T88 and still maintaining satisfactory cell growth for the hybridomas T88 is about pH 6.70 to 7.05. For T88, the most preferred pH is about 6.75.

The methods described herein are independent of the culture methods used and may include: simple batch culture as in T-flasks or roller bottles (Glacken, M. W., et al., 1983, *Trends in Biotechnology*, 1(4), 102-108) or simple batch suspension culture in stirred vessels (Phillips, A. W. et al., 1985, "Experience in the Cultivation of Mammalian Cells on the 8000 L Scale," *Large-Scale Mammalian Cell Culture*, Academic Press, p. 87–95) or airlift vessels (Lambert, K. J. et al., 1987, "Production of Monoclonal Antibodies Using Large-Scale Cell Culture," *Dev. Indust. Microbiology*, 27: 101–106); continuous culture (Ray, N. G. et al., 1989, "Cultivation of Hybridoma Cells in Continuos Cultures: Kinetics of Growth and Product Formation" *Biotechnol Bioeng.*, 33: 724–730); hollow fiber reactors (Altshuler, G. L., et al., 1986, *Biotechnol Bioeng* 28: 646–658); static maintenance reactors (Feder, J., et al., EPA 83870128.2, published 11/7/84); ceramic matrix reactors (Marcipar, A., et al., 1983, *Annals N.Y. Acad Sci*, 413: 416–420); bead immobilized reactors (Nilsson, K., et al., 1983, Nature, 302: 629–630); perfusion reactors (Feder, J., et al., 1985, *American Biotechnol Laboratory* III:24–36) and other culture methods as known in the art.

The pH level can be controlled according to methods known in the art (Reviewed in R. C. Telling and P. J. Radlett, "Large-Scale Cultivation of Mammalian Cells," in *Advances in Applied Microbiology*, Academic Press, New York, 1970, 13: 91–117). For example, the pH can be maintained by means of the bicarbonate/$CO_2$ system. HyClone Lab., Inc., 1987, *Art to Science in Tissue Culture*, 6:1, "The pH acts about Cell Culture."

Other buffering systems can be used with or in place of the bicarbonate system. The most common organic buffer is HEPES (N-Hydroxy-Ethylpiperazine-N'-2-Ethanesulphonic Acid). pH can also be controlled using standard methods from bacterial fermentation, i.e. addition of suitable acid or base in response to a change in pH.

A further advantage of this invention lies in its use of a multi-level pH control strategy to overcome the adverse effect of the low pH on cell growth, in particular the lengthening of the lag phase. As shown in Example 6 below, the multi-level pH control strategy allows the production of sialylated cell products in the presence of high ammonia and yet prevents the lengthening of the lag phase due to the low pH required for such cell products.

It would be apparent to those skilled in the art that the converse is true. For example, these methods also allow the production of a cell product with decreased terminal sialylation by providing an in vitro condition of high level of ammonia at the appropriate pH. Further, it would be apparent to those skilled in the art that the invention can be practiced in any culture condition that produces or has high level of ammonia.

Although any similar or equivalent methods and materials may be employed in the practice or testing of the present invention, the preferred methods and materials are now described. The examples are illustrative of this invention. They are not intended to be limiting upon the scope thereof.

The following examples show how the pH of a cell culture can be manipulated to affect and optimize the glycosylation pattern of a cell product. In particular, the examples below examine the inhibition of sialylation of the antibodies produced by hybridoma T88 by high levels of ammonia in the culture and show how such inhbition can be reversed by manipulating the pH of the culture. They also show how the multi-pH level control strategy can be effectively used to shorten the lag phase and increase the production of antibodies with terminal sialylation in high ammonia culture at low pH.

It would be appreciated by those skilled in the art that the pHs used below are the preferred pHs for the particular cell line, growth conditions, growth phases, the desired glycosylated pattern, in particular, that of terminal sialylation, of the cell product, and other variables. Clearly, the amount of cell products also vary depending on the cell line used. Where these variables are changed, for example, where a different cell line or pattern of glycosylation is desired, those skilled in the art would be able to arrive at the optimal pHs using the guidelines set forth in this patent application.

As a comparison, Example 1 shows that conventional media and culture conditions (i.e. growth without nutrient feeds), result in low final titer of antibodies T88 and low level of ammonia (about 1–6 mM).

Example 2 shows that DM21 together with Nutrient Feeds 1 and 2 result in significantly increased antibody production. However, these novel medium conditions produce high level of ammonia (about 8 mM or above) and a decrease in sialylation of the oligosaccharides of the antibodies produced.

Example 3 shows that when ammonia is gradually added to a culture grown in conventional medium, sialylation is also decreased. This suggests that the high level of ammonia produced in applicant's novel media and nutrient feeds are responsible for the inhibition in sialylation of the cell products.

Example 4 shows that a low culture pH (6.75 versus 7.4) overcomes the inhibition of sialylation by high level of ammonia at low pH. However, the low pH poses the disadvantages of a prolonged lag phase which delays the culture's entry into the growth and antibody production phases.

Example 6 shortens the lag phase by means of a multi-pH level control strategy. The strategy consists of starting the culture at high pH, to prevent a prolonged lag phase; then shifting the culture to a low pH before the ammonia level becomes high. Thus, in the multi-pH level control strategy, the lag phase is shortened, and the production of antibodies with terminal sialylation of oligosaccharides in a high ammonia culture is optimized.

The hybridoma T88 and the antibody it produces are disclosed in U.S. patent application, Ser. No. 057,763, filed June 3 1987, entitled "Gram-Negative Bacterial Endotoxin Blocking Monoclonal Antibodies", by James W. Larrick, et al.. Hybridoma T88 is a mammalian hybridoma which produces human monoclonal antibodies of the IgM class. Briefly, T88 is a trioma produced by somatic cell hybridization using a mouse and human parent hybrid cell line (designated F3B6) and Epstein-Barr Virus (EBV)-transformed human splenocytes. The hybridoma T88 is grown in airlift fermentor as follows, except as specifically stated otherwise in the individual examples.

Setting up of the Airlift Fermentor

A 10 liter working volume airlift fermentor (Chemap; South Plainfield, NJ) equipped with pH and dissolved oxygen probes (all available from Ingold Corp., Andover, MA) and automatic controllers is used. The temperature of the culture in the fermentor is maintained at a constant of 36.5° C. An inlet gas mixture consisting of nitrogen, air or oxygen, and carbon dioxide is sparged into the fermentor at 0.23 liter per minute. The oxygen concentration of the inlet gas is adjusted to maintain the dissolved oxygen concentration at 20% of air saturation. The pH level is controlled by the automatic addition of carbon dioxide to the inlet gas (to lower the pH), or by the addition of 1N sodium hydroxide to the culture (to raise the pH).

The culture media used and any nutrient feed that may be used are specified in each example. Where feeding is called for, the fermentor is set up to add two feed solutions in proportion to the viable cell density, discussed below. The nutrient feeds 1 and 2 are presented below.

TABLE 2

| Nutrient Feed 1 | |
| --- | --- |
| | mg/L |
| L-Arginine.HCl | 2418.8 |
| L-Aspartic Acid | 4000.0 |
| L-Cystine, 2Na salt | 3548.7 |
| L-Glutamic Acid | 2000.0 |
| Glycine | 2000.0 |
| L-Histidine.HCl.H$_2$O | 4053.6 |
| L-Isoleucine | 10000.0 |
| L-Leucine | 5000.0 |
| L-Lysine.HCl | 8000.0 |
| L-Phenylalanine | 3000.0 |
| L-Proline | 1000.0 |
| L-Serine | 3000.0 |
| L-Threonine | 2000.0 |
| L-Tryptophan | 2500.0 |
| L-Tyrosine 2Na.2H$_2$O | 8000.0 |
| L-Valine | 8000.0 |
| Folic Acid | 100.0 |

TABLE 2-continued

| Nutrient Feed 1 | |
| --- | --- |
| | mg/L |
| Sodium Citrate.2H$_2$O | 5880.0 |
| Ferric Chloride: FeCl$_3$.6H$_2$O | 54.0 |
| Ammonium Molybdate 4H$_2$O (NH$_4$)$_6$Mo$_7$O$_{24}$.4H$_2$O | 2.0 |
| Cobalt Chloride: CoCl$_2$.6H$_2$O | 2.0 |
| Cupric Chloride: CuCl$_2$.2H$_2$O | 2.0 |
| Manganous Chloride: MnCl$_2$.4H$_2$O | 2.0 |
| Sodium Selenite: Na$_2$SeO$_3$ | 0.4 |
| Zinc Chloride, anhydrous | 2.0 |
| Monothioglycerol | 100.0 |

TABLE 3

| Nutrient Feed 2 | |
| --- | --- |
| | mg/L |
| L-Asparagine.H$_2$O | 5682.0 |
| L-Glutamine | 29200.0 |
| L-Methionine | 3000.0 |
| Pyruvic Acid, Na salt | 22000.0 |
| Choline Chloride | 1000.0 |
| Inositol | 400.0 |
| Ethanolamine | 200.0 |
| p-Aminobenzoic Acid | 20.0 |
| d-Biotin | 4.0 |
| Pantothenic Acid, Ca salt | 85.0 |
| Nicotinic Acid Amide | 100.0 |
| Pyridoxine.HCl | 20.0 |
| Pyridoxal.HCl | 80.0 |
| Riboflavin | 10.0 |
| Thiamine HCl | 100.0 |
| Vitamin B-12 | 40.0 |

Where ammonia is called for in the examples, ammonia is added daily as ammonium chloride (0.5M) by peristaltic pump, based on the desired concentration profile in the examples.

Before inoculation, the fermentor is set at a steady state in terms of temperature, pH and dissolved oxygen level. The glutamine content of the DM21 (prior to addition of any feeds) used is 8 mM. The fermentor is inoculated with rapidly dividing midexponential phase T88 cells (approximately 6 to $12 \times 10^5$ viable cells/ml), to an initial density of approximately $1 \times 10^5$ viable cells/ml.

The total cell density is measured daily with a Model ZF Coulter Counter (Coulter Electronics: Hidleah, FL.), and viability determined by hemocytometer using trypan blue dye exclusion. Where feeding is called for in the examples, the overall volumetric addition rates of nutrient feeds 1 and 2 are adjusted based on the viable cell density. The nutrient feeds 1 and 2 are each added to the 10 L fermentor at 5 ml per day per $10^9$ viable cell.

Glucose (500 g/L) is fed daily to the fermentor to maintain a concentration of 1 to 6 g/L. In all the examples, glucose feeding is used. The glucose level in the fermentor is monitored by off-line samples assayed with a YSI model 23A glucose analyzer (Yellow Springs Instrument Co. Inc.: Yellow Springs, Ohio).

The experiment in each example is repeated to obtain the range for each of the factors presented in the Result section.

Analysis of Antibody Yield

The antibody yield from the cell culture can be determined by techniques known in the art, for example, enzyme-linked immuno-adsorbent assay (ELISA) using a standard IgM ELISA.

Analysis of the Glycosylation Pattern of the Antibody

The glycosylation pattern, in particular, the degree of sialylation of a glycoprotein can be analyzed using methods known in the art, for example, as presented in Rademacher, H., et al., 1986, *Biochem. Soc. Symp.*, (Eng.), 51:131–48, "Immunoglobulin G as a Glycoprotein", and Parekh, R. B. et al., 1985, *Nature* 316:452, "Association of Rheumatoid Arthritis and Primary Osteoarthritis with Changes in the Glycosylation Pattern of Total Serum IgG." The following outlines the preferred method for determining the degree of sialylation of the antibody T88. First, the antibody is purified. The preferred purification procedure is disclosed in U.S. patent application, Ser. No. 474,142, filed Feb. 2, 1990, "Production of Monoclonal Antibodies with Reduced Clearance Rate" to Winkelhake, J. L., et al. The details of the following steps are disclosed in Rademacher and Parekh, above; any modifications in lieu of the particular T88 IgM used herein can be arrived at by those skilled in the art. The antibody fraction is exhaustively dialyzed to render it free of salt and soluble sugar. The oligosaccharides are released from the antibody by controlled hydrazinolysis. The oligosaccharides are then radioactively labelled by reduction with $NaB_3H_4$. The reduced oligosaccharides are fractionated based on their charges by high-voltage paper electrophoresis. Fractions of the oligosaccharides which are sialylated are estimated by the ratio of the area of the first (uncharged) peak, to the total area of the other (charged) peaks.

To confirm that all the charged species are due to sialic acid; before the electrophoresis step, the oligosaccharides are pretreated with neuraminidase, preferably highly purified neuraminidase, and exhaustively dialyzed to remove the terminal sialic acid. The electrophoresis is then repeated and all the oligosaccharides migrate as a single (uncharged) peak.

EXAMPLE 1

Production of Antibody T88 Using Conventional Medium

Hybridoma T88 is grown in commercially available and widely used serum-free HL-1 medium (Ventrex Labs, Portland, ME) supplemented with the typical 4 mM of glutamine. Using the airlift fermentor set-up described above, the pH of the culture is maintained at pH 7.4.

Result

The lag phase of the culture is between 0 to 10 hours, and the culture longevity is between 5 to 10 days. The maximum viable cell density is between 0.8 to $2.0 \times 10^6$/ml. The final antibody T88 titer is between 30 to 70 mg/L. The final ammonia level is between 1 to 6 mM. The sialylation pattern on high voltage paper radioelectrophoretogram is noted. This is the desired sialylation pattern and is the standard to which the following examples would be compared to.

EXAMPLE 2

Production of Antibody T88 Using DM21

This Example uses DM-21 medium supplemented with 8 mM glutamine, and the cells are fed with nutrient feeds 1 and 2, and 500 g/L glucose. (The compositions of DM-21, nutrient feeds 1 and 2 are presented in Tables 1,2, and 3 above, respectively). The pH of the culture is maintained at pH 7.4.

Result

Similar to Example 1, the lag phase of the culture is between 0 to 10 hours. However, with the DM21 and nutrient feeds, the culture longevity is increased to between 12 to 18 days. Similarly, an increased in maximum viable cell density is seen with 1.4 to $3.0 \times 10^6$/ml. Most significantly, the final antibody T88 titer is greatly increased to between 200 to 350 mg/L. However, the trade-off for increases in antibody production, culture longevity, and cell density is the increase in final ammonia level to between 8 to 15 mM, due to an increase in the glutamine and alanine in the DM-21 medium, and the glutamine supplement in feed 2. Corresponding with this increased in ammonia level, the terminal sialylation of the oligosaccharide of the antibody is inhibited, resulting in the reduction in the ratio of peaks with charged versus uncharged species of the oligosaccharides compared to Example 1.

EXAMPLE 3

The Effect of Ammonia Addition

To determine whether the decreased in sialylation of the antibody in Example 2 is due to ammonia, the experiment in Example 1 is duplicated except that ammonium chloride is gradually added over the culture, to reach the final ammonia level similar to that of Example 2.

Result

The lag phase of the culture is between 0 to 10 hours, and the culture longevity is between 5 to 9 days. The maximum viable cell density is between 0.7 to $1.8 \times 10^6$/ml. The final antibody T88 titer is between 30 to 70 mg/L. The final ammonia level is between 8 to 15 mM. Terminal sialylation is inhibited at a similar level as that of Example 2, that is the ratio of peaks with charged versus uncharged species of the oligosaccharides is reduced compared to Example 1.

Thus the result confirms that the sialylation pattern of the antibody is altered by a high level of ammonia in the medium. The lag phase, culture longevity, maximum viable cell density, and final antibody titer closely follow that of Example 1, showing that they are dependent on the composition of the culture medium.

EXAMPLE 4

The Effect of Low pH in Overcoming Inhibition of Sialylation of Antibody Due to High Level of Ammonia The following experiment shows that lowering the pH would overcome the inhibition of sialylation of the antibody by ammonia. To do so, the experiment in Example 2 is duplicated, but the pH is maintained at a lower level of 6.75.

Result

The lag phase of the culture is between 10 to 40 hours, and the culture longevity is between 13 to 20 days. The maximum viable cell density is between 1.2 to $2.4 \times 10^6$/ml. The final antibody T88 titer is between 200 to 350 mg/L. The final ammonia level is between 8 to 18 mM. The degree of sialylation is similar to that of Example 1.

Comparing the lag phase of Example 4 to the previous Examples shows that at a low pH, the lag phase is prolonged. This poses a problem because the culture takes a longer time to reach growth and production phases. On the other hand, compared to Example 2, the lower pH has the advantage of allowing production of antibody with normal degree of sialylation. The lower pH overcomes the inhibition of terminal sialylation by ammonia.

EXAMPLE 5

The Effect of Low pH in Conventional Culture Medium with Added Ammonium Chloride To further confirm that lower pH can overcome the inhibitory effect on terminal sialylation by high levels of ammonia added to a conventional medium, this Example duplicates the experiment of Example 3, but with the pH maintained at the lower level of 6.75.

Result

The lag phase of the culture is between 10 to 40 hours, and the culture longevity is between 5 to 10 days. The maximum viable cell density is between 0.6 to $1.5 \times 10^6$/ml. The final T88 antibody titer is between 30 to 70 mg/L. The final ammonia level is between 8 to 15 mM. The degree of sialylation is similar to that of Example 1.

The above result, along with the result of Example 2, confirms that high level of ammonia affects terminal sialylation, independent of the culture medium used. Further, the ammonia effect can be overcome by a lower pH.

EXAMPLE 6

Multi-Level pH Control Strategy as Applied to Production of T88 Antibody with Terminal Sialylation In view of the above results, the multi-level pH control strategy is devised which maximizes the production and yield of sialylated T88, and yet avoids the prolonged lag phase of Examples 4 and 5. The strategy is as follows: the cells are grown under the same conditions as Example 4, except that at 0 hour the cells are inoculated at pH 7.2. Then from 75 to 90 hours, the pH of the culture medium is gradually ramped to 6.75.

Result

The result shows that the multi-level pH control strategy achieves the optimum desirable results found in the other Examples and avoids their disadvantages. Compared to the other Examples, the lag phase is at the minimum of 0 to 10 hour, and the longevity of the culture at the high of between 13 to 20 days. The maximum viable cell density is at the optimal of between 1.4 to $3.0 \times 10^6$/ml. The final antibody titer is at the maximum yield of 200 to 350 mg/L. Despite the presence of high ammonia levels of 8-18 mM, the degree of sialylation of the antibodies produced is similar to that of Example 1.

The present invention has been described with reference to specific embodiments. However, this application is intended to cover those changes and substitutions which may be made by those skilled in the art without departing from the spirit and the scope of the appended claims. Further, various modifications of the invention in addition to those shown and described herein apparent to those skilled in the art from the preceding description are considered to fall within the scope of the appended claims.

We claim:

1. A method for increasing the production of terminally sialylated secreted monoclonal antibody by antibody secreting cells in a cell culture which comprises ammonia at about 6 mM or above, comprising the steps of:
   a) growing monoclonal antibody secreting cells in a culture medium comprising ammonia at about 6 mM or above;
   b) growing the cells during the growth phase, at a pH of 7.2-7.4 which favors optimal cell growth;
   c) gradually decreasing the pH of the cell culture to 6.7-7.05 which favors increased production of terminally sialylated monoclonal antibody, as the cell culture approaches pseudo-stationary phase;
   d) maintaining the pH during the production phase at 6.70-7.05; and
   e) harvesting the monoclonal antibody.

2. A method as described in claim 1, wherein said monoclonal antibody secreting cells are hybridoma cells that secrete the monoclonal antibody T88.

* * * * *